United States Patent
De Vries et al.

(10) Patent No.: US 11,937,052 B2
(45) Date of Patent: Mar. 19, 2024

(54) FITTING AGENT FOR A HEARING DEVICE AND METHOD FOR UPDATING A MULTI-ENVIRONMENT USER MODEL

(71) Applicant: GN Hearing A/S, Ballerup (DK)

(72) Inventors: Aalbert De Vries, Eindhoven (NL); Tanya Ignatenko, Eindhoven (NL); Kirill Kondrashov, Eindhoven (NL)

(73) Assignee: GN HEARING A/S, Ballerup (DK)

( * ) Notice: Subject to any disclaimer, the term of this patent is extended or adjusted under 35 U.S.C. 154(b) by 123 days.

(21) Appl. No.: 17/744,203

(22) Filed: May 13, 2022

(65) Prior Publication Data
US 2022/0400350 A1 Dec. 15, 2022

(30) Foreign Application Priority Data
Jun. 15, 2021 (DK) .............................. PA 202100638

(51) Int. Cl.
*H04R 25/00* (2006.01)
*A61B 5/12* (2006.01)

(52) U.S. Cl.
CPC ............. *H04R 25/70* (2013.01); *A61B 5/123* (2013.01); *H04R 25/30* (2013.01); *H04R 25/505* (2013.01); *H04R 2225/41* (2013.01)

(58) Field of Classification Search
CPC .... A61B 5/123; H04R 2225/41; H04R 25/70; H04R 25/505; H40R 25/30
See application file for complete search history.

(56) References Cited

U.S. PATENT DOCUMENTS

2016/0112795 A1 * 4/2016 Bach ..................... H03M 3/356
341/143

FOREIGN PATENT DOCUMENTS

| EP | 3493555 A1 * | 6/2019 | ............. H04R 25/30 |
| WO | WO-2019195866 A1 * | 10/2019 | ............. H04R 25/43 |
| WO | WO-2020144160 A1 * | 7/2020 | ............ H04R 25/505 |

* cited by examiner

*Primary Examiner* — Sean H Nguyen
(74) *Attorney, Agent, or Firm* — Vista IP Law Group, LLP

(57) ABSTRACT

A method for updating a user model and fitting agent for a hearing device system is disclosed, the hearing device system comprising a hearing device worn by a hearing device user, wherein the fitting agent comprises one or more processors configured to initialize a user model comprising a plurality of user preference functions and associated user response distributions, wherein each user preference function is associated with an environment; obtain environment data indicative of a present environment; obtain a test setting comprising a primary test setting and a secondary test setting for the hearing device; present the test setting to the hearing device user; obtain a user input of a preferred test setting indicative of a preference for either the primary test setting or the secondary test setting; and update the user model based on hearing device parameters of the preferred test setting and the environment data.

18 Claims, 3 Drawing Sheets

FITTING AGENT FOR A HEARING DEVICE AND METHOD FOR UPDATING A MULTI-ENVIRONMENT USER MODEL

RELATED APPLICATION DATA

This application claims priority to, and the benefit of, Danish Patent Application No. PA 202100638 filed on Jun. 15, 2021. The entire disclosure of the above application is expressly incorporated by reference herein.

FIELD

The present disclosure relates to hearing devices and related tools, methods, and systems in particular for one or more of determining, tuning, fitting and optimizing hearing device parameters. Thus, a fitting agent for a hearing device and related methods, in particular a method for updating a user model, are provided.

BACKGROUND

Fitting and tuning of hearing devices or hearing aids has always been considered a tedious task of healthcare professionals (HCPs). Traditional approaches for fitting hearing device parameters rely on compensation of a user's hearing loss, based on audiograms, by applying rules such as NAL-NL1 or NAL-NL2. These rules, however, do not take into account specific user preferences.

Recent approaches involve preference learning for hearing devices.

EP 3 493 555 A1 relates to a method for tuning hearing device parameters of a hearing device and a hearing device. The method comprises initializing a model; obtaining an initial test setting defined by one or more initial test hearing device parameters; assigning the initial test setting as a primary test setting; obtaining a secondary test setting based on the model; outputting a primary test signal according to the primary test setting; outputting a secondary test signal according to the secondary test setting; detecting a user input of a preferred test setting; updating the model based on the primary test setting, the secondary test setting, and the preferred test setting; and in accordance with a determination that a tuning criterion is satisfied, updating the hearing device parameters of the hearing device based on hearing device parameters of the preferred test setting.

SUMMARY

Challenges still remain in improving the tools, methods and devices allowing an improved fitting and tuning of hearing device parameters.

A fitting agent is disclosed, the fitting agent optionally being for a hearing device system comprising a hearing device worn by a hearing device user. The fitting agent comprises one or more processors configured to initialize a user model comprising one or a plurality of user preference functions, optionally with associated distributions of preference function parameters, and associated user response distributions, wherein each user preference function is optionally associated with an environment; obtain environment data indicative of a present environment; obtain a test setting comprising a primary test setting and a secondary test setting for the hearing device; present the test setting to the hearing device user; obtain a user input of a preferred test setting indicative of a preference for either the primary test setting or the secondary test setting; and update the user model, e.g., based on hearing device parameters of the preferred test setting and/or the environment data.

Also, a method for updating a user model for a hearing device user is disclosed, wherein the method comprises initializing a user model comprising one or a plurality of user preference functions, optionally with associated distributions of preference function parameters, and associated user response distributions, wherein each user preference function is optionally associated with an environment; obtaining environment data indicative of a present environment; obtaining a test setting comprising a primary test setting and a secondary test setting for the hearing device; presenting the test setting to the hearing device user; obtaining a user input of a preferred test setting indicative of a preference for either the primary test setting or the secondary test setting; and updating the user model, e.g., based on hearing device parameters of the preferred test setting and/or the environment data.

The present disclosure takes into account any differences in user preference in different environments and provides effective and memory-efficient user preference model update. In particular, the need for storing historical and specific user feedback (previous primary and secondary test settings and preference thereof) may be eliminated in turn reducing the memory requirements.

Further, environment-dependent user preference functions may provide simpler user preference functions in turn allowing a simple and effective way to configure one or more hearing device parameters of a hearing device. Further, the present disclosure provides an improved listening experience to the user by improving the modelling of the users preferred hearing parameter settings in different environments in turn resulting in optimized settings being applied in the hearing device, which in turn allows for an improved user experience.

Further, the present disclosure provides an efficient automated search for optimal hearing device parameters by incorporating a user feedback into the learning cycle. A fitting agent, devices, and methods are provided, that allows to learn user preferences for hearing device parameters in an efficient and minimally obtrusive way by empowering the user to take direct decisions and have direct impact on the fitting and/or tuning process.

Further, the present disclosure allows that hearing device parameters can be configured, such as fitted and/or tuned, during a normal operating situation and/or with a small number of user inputs/interactions. Thus, a simple and smooth user experience of the hearing device is provided.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Figure 1:
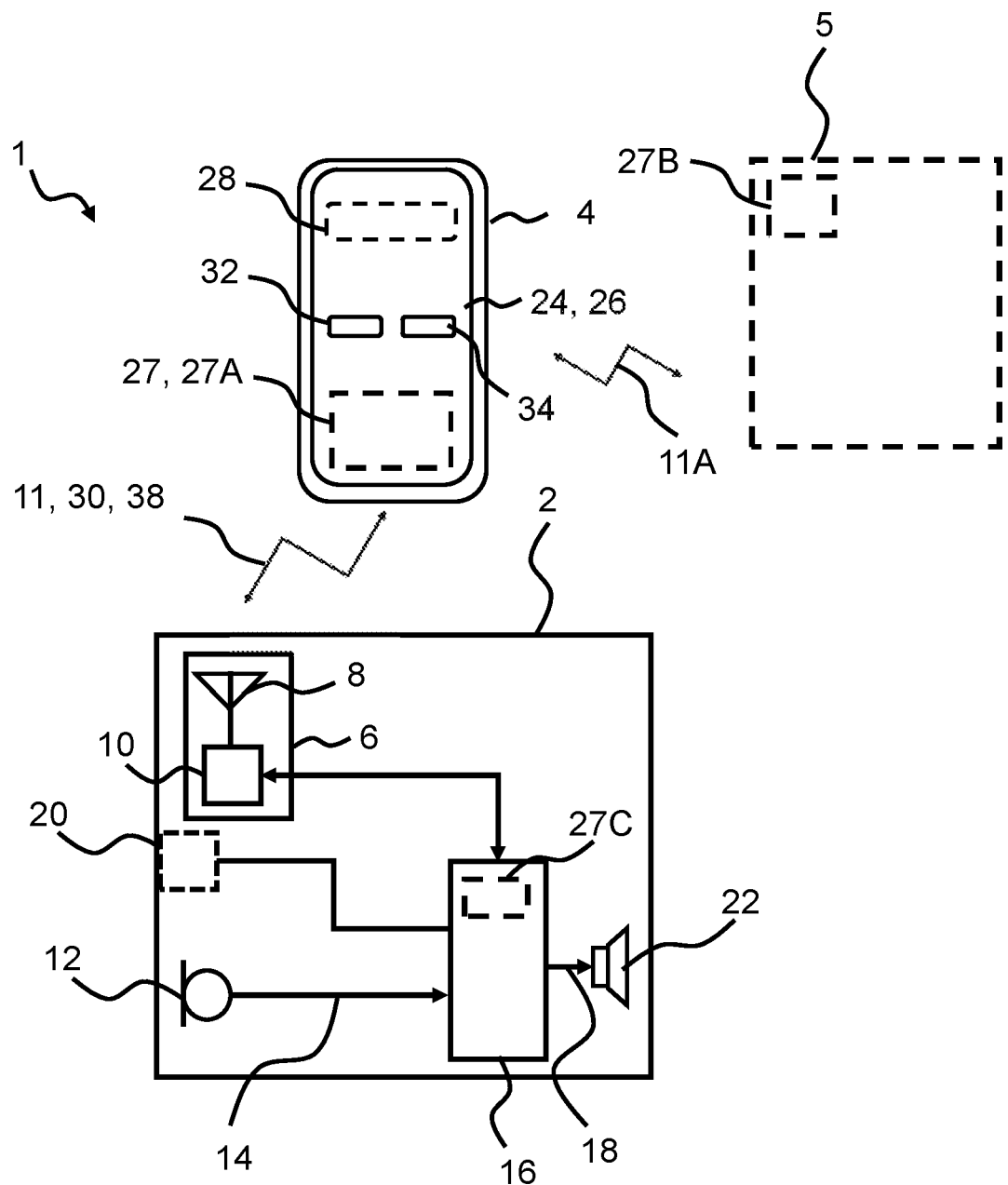
FIG. 1 schematically illustrates a hearing system according to the present disclosure.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

A fitting agent is disclosed. The fitting agent or at least a first part thereof may be implemented, e.g. as an application, in an accessory device, such as an electronic device. The accessory device comprises an interface, a processor, and a memory. The accessory device may for example be or comprise a mobile phone, such as a smartphone, a smartwatch, a special purpose device, a computer, such as a laptop computer or PC, or a tablet computer. The fitting agent or at least a second part thereof may be implemented in a server device. The fitting agent or at least a third part thereof may be implemented in a hearing device.

The present disclosure relates to a hearing device system, fitting agent, accessory device and hearing device of the hearing device system, and related methods. The accessory device forms an accessory device to the hearing device. The accessory device is typically paired or wirelessly coupled to the hearing device. The hearing device may be a hearing aid, e.g. of the behind-the-ear (BTE) type, in-the-ear (ITE) type, in-the-canal (ITC) type, receiver-in-canal (RIC) type, receiver-in-the-ear (RITE) type, or microphone-and-receiver-in-the-ear (MaRIE) type. The hearing device may be a hearable, such as a pair of earbuds or a headset. Typically, the hearing device system is in possession of and controlled by the hearing device user.

The hearing device system may comprise a server device and/or a fitting device. The fitting device is controlled by a dispenser and is configured to determine configuration data, such as fitting parameters. The server device may be controlled by the hearing device manufacturer.

The fitting agent may be a fitting agent for a hearing device system comprising a hearing device worn by a hearing device user.

The fitting agent comprises one or more processors. The one or more processors are configured to initialize a user model comprising one or a plurality of user preference functions, optionally with associated preference function parameter distributions, and optionally associated user response distributions. Each user preference function is optionally associated with an environment, such as an acoustic environment.

The fitting agent, such as one or more processors of the fitting agent, is configured to obtain environment data indicative of a present environment. The environment data may comprise signal vector or signal matrix denoted s of one or more input signals and/or other contextual information or any parameter determined based thereon, such as signal-to-noise ratio (SNR) and power.

An environment, such as an acoustic environment, may be characterized by one or more of a first environment parameter, such as input signal level or input power, and a second environment parameter, such as SNR, for one or more input signals. In other words, the environment data may comprise a (first) SNR and/or a (first) power of a (first) input signal. Thus, to obtain environment data indicative of a present environment may comprise to obtain, such as determine or receive, one or more environment parameters optionally including a (first) SNR and/or a (first) power of a (first) input signal.

The fitting agent, such as one or more processors of the fitting agent, is configured to obtain, such as one or more of determine, receive, and retrieve, a test setting comprising a primary test setting and/or a secondary test setting for the hearing device.

The fitting agent, such as one or more processors of the fitting agent, is configured to present the test setting to the hearing device user. The fitting agent is configured to present the test setting to the hearing device user. To present the test setting to the hearing device user comprises presenting the primary test setting and/or the secondary test setting to a user. To present the primary test setting and the secondary test setting to a user optionally comprises to output a primary test signal according to the primary test setting. The primary test signal may be an audio signal. The primary test signal may be output via loudspeaker or receiver of a hearing device. To present the primary test setting and the secondary test setting to a user optionally comprises to generate the primary test signal according to the primary test setting in accessory device and to stream the primary test signal from accessory device to hearing device. To present the primary test setting and the secondary test setting to a user optionally comprises to transmit a control signal indicative of primary test signal/primary test setting from accessory device to hearing device. The control signal may include primary test setting. To present the primary test setting and the secondary test setting to a user may comprise to generate the primary test signal according to the control signal in the hearing device, e.g. based on primary test setting of the control signal.

To present the primary test setting and the secondary test setting to a user optionally comprises to output a secondary test signal according to the secondary test setting. The secondary test signal may be an audio signal. The secondary test signal may be output via loudspeaker or receiver of a hearing device. To present the primary test setting and the secondary test setting to a user optionally comprises to generate the secondary test signal according to the secondary test setting in accessory device and to stream the secondary test signal from accessory device to hearing device. To present the primary test setting and the secondary test setting to a user optionally comprises to transmit a control signal indicative of secondary test signal/secondary test setting from accessory device to hearing device. The control signal may include secondary test setting. To present the primary test setting and the secondary test setting to a user may comprise to generate the secondary test signal according to the control signal in the hearing device, e.g. based on secondary test setting of the control signal.

The fitting agent is configured to obtain a primary test setting also denoted x_ref or $x^{ref}$ for the hearing device. The primary test setting x_ref is a vector comprising M hearing device parameters for the hearing device. The hearing device parameters may comprise one or more of filter coefficients, compressor settings, gains, or other parameters relevant for the operation of or signal processing in the hearing device. The primary test setting may be based on and/or dependent on the present environment. In other words, the primary test setting may be based on and/or dependent on the environment data. The primary test setting may be based on and/or dependent on one or more environment probabilities including a first environment probability ENVP_1 indicative of the present environment being a first environment and/or a second environment probability ENVP_2 indicative of the present environment being a second environment. The primary test setting may be a weighted combination (with environment probabilities as weights ENVP_k) of test settings for the environments ENV_k, k=1, 2, . . . , K.

The fitting agent is configured to obtain a secondary test setting also denoted x_alt or $x^{alt}$ for the hearing device. The secondary test setting x_ref is a vector comprising M hearing device parameters for the hearing device. The hearing device parameters may comprise one or more of filter coefficients, compressor settings, gains, or other parameters relevant for the operation of or signal processing in the hearing device. The secondary test setting may be based on and/or dependent on the present environment. The secondary test setting may be based on and/or dependent on the present environment. In other words, the secondary test setting may be based on and/or dependent on the environment data. The secondary test setting may be based on and/or dependent on one or more environment probabilities including a first environment probability ENVP_1 indicative of the present environment being a first environment and/or a second environment probability ENVP_2 indicative of the present environment being a second environment. The secondary test setting may be a weighted combination (with environment probabilities as weights ENVP_k) of test settings for the environments ENV_k, k=1, 2, . . . , K.

The fitting agent, such as one or more processors of the fitting agent, is configured to obtain, such as receive and/or detect, a user input of a preferred test setting indicative of a preference for either the primary test setting or the secondary test setting.

The non-preferred test setting is the primary test setting or the secondary test setting not being selected as a preferred test setting. Accordingly, a hearing device and/or accessory device(s) implementing the fitting agent or at least a part of the fitting agent may comprise one or more user interfaces for obtaining, such as receiving and/or detecting, a user input. For example, the hearing device may comprise a user interface receiving a user input. The user interface of the hearing device may comprise one or more buttons, an accelerometer and/or a voice control unit. The accessory device may comprise a user interface. The user interface of the accessory device may comprise a touch sensitive surface, e.g. a touch display, and/or one or more buttons. The user interface of the accessory device may comprise a voice control unit. The user interface of the hearing device may comprise one or more physical sliders, knobs and/or push buttons. The user interface of the accessory device may comprise one or more physical or virtual (on-screen) sliders, knobs and/or push buttons.

The fitting agent is configured to obtain, such as detect, a user input of a preferred/selected test setting indicative of a preference for either the primary test setting or the secondary test setting. In the fitting agent, to detect a user input of a preferred test setting indicative of a preference for either the primary test setting or the secondary test setting may comprise prompting the user for the user input, e.g. by a beep tone signal or voice signal from the hearing device and/or a visual, haptic and/or audio prompt from an accessory device. Detecting a user input may be performed on the hearing device, e.g. by a user activating a button and/or an accelerometer (e.g. single or double tapping the hearing device housing) in the hearing device. To detect a user input may be performed on an accessory device, e.g. by a user selecting a user interface element representative of the preferred test setting, e.g. on a touch-sensitive display of the user accessory device.

The method or at least parts thereof may be performed in one or more electronic devices, such as a hearing device and/or accessory device(s). The method or at least parts thereof may be performed in an accessory device or a plurality of accessory devices, such as in a smartphone optionally in combination with a smartwatch. The method may be a computer-implemented method. The fitting agent/method may be for/part of one or more of optimizing, determining, fitting, tuning, and modelling, such as determining hearing device parameters of a hearing device. Performing part(s) of the method in accessory device(s), such as a smartphone optionally in combination with a smartwatch, may be advantageous in providing a more smooth user input and user experience. Further, performing part(s) of the method in accessory device(s) may be advantageous in providing a more power efficient method from the perspective of the hearing device. The method or at least parts thereof may be performed in a server device and/or in a fitting device.

The present disclosure relates to a fitting agent for a hearing device, and in particular to a fitting agent for one or more of optimizing, determining, fitting, and tuning hearing device parameters of a hearing device.

The user model optionally represents one or a plurality of probabilistic descriptions of user responses, when comparing two sets of hearing device parameter settings. Integral parts of the user model include one or more, such as a plurality of user preference functions and one or more, such as a plurality of distributions of the user responses to the presented choices of parameters. The user model comprises one or more distributions of parameters of the respective user preference functions. In other words, each user preference function has an associated distribution of hearing device parameters. In other words, the user model may include a first user preference function and associated first user response distribution, wherein the first user preference function is optionally associated with a first environment. The user model may include a second user preference function and associated second user response distribution, wherein the second user preference function is optionally associated with a second environment. The user model may include a third user preference function and associated third user response distribution, wherein the third user preference function is optionally associated with a third environment. The user model may include K user preference functions and associated user response distribution, wherein the k'th user preference function, k=1, 2, . . . , K is optionally associated with a k'th environment.

A vector of hearing device parameters is optionally defined on an M-dimensional continuous compact surface. In particular, hearing device parameters x are optionally defined on an M-dimensional hyper-cube, i.e., $x \in [0,1]^M$. In one or more exemplary fitting agents/methods, the hearing device parameters may be normalized by their physical range. The fitting agent/method, is configured to find optimized/improved values of hearing device parameters, also denoted θ for a particular user. The number M of hearing device parameters may be 1 and/or less than 100, such as in the range from 10 to 50. The number M of hearing device parameters may be larger than 20, such as in the range from 25 to 75.

In general, the user preference functions are unknown. The user preference functions $f(x, \theta, \Lambda, k) = f(x; \theta_k, \Lambda_k)$, k=1, 2, . . . , K, where K is the number of user preference functions, may be parametric functions of hearing device parameters $x \in [0,1]^M$ with known form but unknown shape. This shape is optionally characterized by fitting or tuning parameters, $\theta_k \in [0,1]^M$ and a scaling matrix $\Lambda_k$. The scaling matrix $\Lambda_k$ may be a positive-definite scaling matrix $\Lambda_k$. The scaling matrix may be a diagonal matrix $\Lambda_k = \text{diag}([\lambda_1, \lambda_2, \ldots, \lambda_M])$, $\lambda_m \in \mathbb{R}^+$, $m=1, 2, \ldots, M$.

The user preference functions or at least one or more of the user preference functions of the K user preference functions may be unimodal.

In one or more exemplary fitting agents/method, distribution priors may be applied to each element of $\Lambda_k$. For example, Lognormal distribution priors may be applied to each element of $\Lambda_k$, e.g., $\log(\lambda_m) \sim \mathcal{N}(\mu_m, \sigma_m^2)$ or Gamma distribution priors may be applied to each element of $\Lambda$, e.g., $\lambda_m \sim \text{Gamma}(\alpha_m, \beta_m)$.

The scaling matrix $\Lambda_k$ does not need to be a diagonal matrix. The scaling matrix $\Lambda_k$ may be selected as $\Lambda_k = L'*L$, where L is a low-triangular matrix (also known as the Cholesky decomposition of $\Lambda_k$). Gaussian priors may be applied on each of the elements of L, e.g., $L_{ij} \sim \mathcal{N}(\mu_{ij}, \sigma_{ij}^2)$.

The maximizing argument $\theta_k$ of a k'th environment may be a transformation of another variable, e.g. may be constrained by the following prior assumptions $$\theta_k = \Phi(\hat{Y}), \quad (2)$$

where $\Phi(\hat{Y})$ is a cumulative density function of a probability distribution, such as the standard normal distribution, and $\hat{Y}$ is a sample from another probability distribution.

In one or more example fitting agent/methods, the maximizing argument $\theta_k$ may be constrained by the following assumptions on representing $\theta_k$ as a transformation of $\hat{Y}$ and corresponding prior distribution of the transformed variable:

$$\theta_k = \Phi(\hat{Y}), \text{ with } \hat{Y} \sim \mathcal{N}(\mu_k, \Sigma_k), \quad (3)$$

where $\Phi(\hat{Y}) = \int_{-\infty}^{\hat{Y}} \mathcal{N}(x|0,1)dx$ is the cumulative density function of the standard normal distribution, and $\hat{Y}$ is a sample from the normal distribution with mean vector $\mu_k$ and covariance matrix $\Sigma_k$. Values of the mean and covariances may be learned from the user responses.

In one or more example fitting agents/methods, the scaling matrix may be a transformed scaling matrix, e.g. by applying a log transform to the elements of the scaling matrix.

The user preference functions may be denoted $f$ or $f_k(x; \theta_k, \Lambda_k)$, where each user preference function $f_k(x; \theta_k, \Lambda_k)$ is associated with environment k of K environments/user preference functions. The user preference functions $f_k(x; \theta_k, \Lambda_k)$ may be given by:

$$f_k(x; \theta_k, \Lambda_k) = -((x-\theta_k)^T \Lambda_k (x-\theta_k))^\nu, \quad (1)$$

where x is an M-dimensional vector optionally in the hypercube $[0,1]^M$ and that represents the (M) hearing device parameters of the device in the k'th environment, $\theta_k$ is the maximizing argument of $f_k$, $\Lambda_k$ is a positive definite M×M scaling matrix characterizing user sensitivity to hearing device parameter changes, M is an integer, and v is a real-valued exponent. The real-valued exponent v may be in the range from 0.01 to 0.99. The real-valued exponent v may be less than 0.5 such as in the range from 0.01 to 0.45. The real-valued exponent v may be larger than 0.5 such as in the range from 0.55 to 0.99. In one or more exemplary fitting agents/methods, the real-valued exponent v may be in the range from 0.25 to 0.75, such as 0.5.

The user preference functions $f_k(x; \theta_k, \Lambda_k)$ may be given by:

$$f(x; \theta_k, \Lambda_k) = \exp(-(x-\theta_k)^T \Lambda_k (x-\theta_k))^\nu.$$

The variables $\theta_k, \Lambda_k$ are also denoted user preference function parameters, where $\theta_k$ is an optimum of the user preference function that corresponds to the optimal user-specific HA parameters and $\Lambda_k \in \mathcal{R}^{D \times D}$ is a diagonal matrix indicative of a user sensitivity, i.e. ability to distinguish change in the parameter. It is noted that other unimodal user preference functions are also possible.

The fitting agent/one or more processors of the fitting agent is/are configured to update the user model, such as one or more user preference functions $f_k(x; \theta_k, \Lambda_k)$ and/or one or more user response distributions $P_u$, based on hearing device parameters of the preferred test setting and the environment data. In other words, a user response distribution $P_u$, may model a user response in one or more environments. A user response distribution may be a weighted user response distribution for all or a subset of the K environments, e.g. where the weights are based on environment probabilities ENVP_k, $k=1, \ldots, K$ and distributions of parameters of the user preference functions $f_k(x; \theta_k, \Lambda_k)$.

The fitting agent is configured to update the user model based on hearing device parameters of the preferred test setting, a non-preferred test setting and optionally the environment data. In particular, the fitting agent may be configured to update the user model based on (r, x_ref, x_alt, s). To update the user model may comprise to update the user preference function, or at least parameters thereof and/or to update parameter distributions associated with user preference functions, based on environment data and one or more of the primary test setting, the secondary test setting and the user input of a preferred test setting. In other words, the parameters of the user preference function and/or associated parameter distributions may be updated based on the result of the trial including the primary test setting, the secondary test setting, the preferred test setting of the primary test setting and the secondary test setting, and environment data. To update the user model may comprise to update the user response distribution(s), or at least parameters thereof, based on environment data and one or more of the primary test setting, the secondary test setting and the user input of a preferred test setting. In other words, the parameters of the user preference function may be updated based on the result of the trial including the primary test setting, the secondary test setting, the preferred test setting of the primary test setting and the secondary test setting, and environment data. To update the user model may comprise to update the user response distribution(s), or at least parameters thereof, based on one or more environment probabilities optionally including a first environment probability and a second environment probability. Thus, to update the user model may comprise to update the parameter distribution(s) of user preference function parameters $\theta_k$ and/or $\Lambda_k$, based on environment data and one or more of the primary test setting, the secondary test setting and the user input of a preferred test setting. In other words, the parameters distributions associated with the user preference functions may be updated based on the result of the trial including the primary test setting, the secondary test setting, the preferred test setting of the primary test setting and the secondary test setting, and environment data. To update the user model, such as to update the parameter distribution(s) of user preference function parameters $\theta_k$ and/or $\Lambda_k$, may comprise to update the parameter distribution(s) of user preference function parameters $\theta_k$ and/or $\Lambda_k$, based on one or more environment probabilities optionally including a first environment probability and a second environment probability.

In one or more exemplary fitting agents and/or methods, to update the user model may be based on Bayesian inference. Updating the user model may comprise updating one or more of the parameters of the user preference function and/or user response distribution(s) and/or environmental model and/or parameter distributions associated with the user preference functions. Updating the user model may comprise to determine one or more posteriors of parameters of the user preference function(s).

To update the user model may comprise to determine a posterior of the parameters of one or more of, such as a subset of or all the user preference functions, e.g. based on the environment data, a previous parameter posterior, such as the last or current parameter posterior, preferred test setting, and a non-preferred test setting.

Thus, the user preference function for the k'th environment may be given as:

$$f_k(x;\theta_k,\Lambda_k) = -\sqrt{(x-\theta_k)^T \Lambda_k (x-\theta_k)}. \quad (4)$$

The tuning parameters correspond to the location of the optimum of the function, $\theta_k$, which is the optimal hearing device parameters for a user; and to the spread around this optimum, $\Lambda_k$, that characterizes user sensitivity to hearing device parameter changes, respectively. The tuning parameters are user-specific and need to be learned in order to provide an optimum or improved user experience. The form of this user preference function has an attractive property that allows for quick narrowing of the search space.

The user model, such as one or more user preference functions, is optionally based on a first assumption and/or a second assumption. The first assumption may be that the user preference functions are unimodal preference functions representative of preference of a user. The second assumption may be that the user can be uncertain about preference, which may be expressed in terms of an additive random variable. A value function $u_k(\cdot)$ may be defined in order to model user preference uncertainty. The value function $u_k(\cdot)$ may be defined as $$u_k(x) = f_k(x;\theta_k,\Lambda_k) + \varepsilon_k, \quad (5)$$

where the user uncertainty error $\varepsilon_k$ is optionally assumed to have a Gaussian distribution, such as the standard Gaussian distribution, e.g.

$$\varepsilon_k \sim \mathcal{N}(0,1) \quad (6)$$

The variance of the Gaussian distribution may be a real value, e.g. in the range from 0 to 1 or larger than 1.

A trial for a user defines a pair of test settings including a primary test setting and a secondary test setting. A user response is obtained to a user's pairwise comparison of test settings from a trial, defined by a pair {x_ref, x_alt} of test settings, where the primary test setting x_ref and the secondary test setting x_alt are the so-called reference and alternative parameter proposal, respectively. In other words, a trial T_n also denoted $D_n$ is performed, where each trial T_n comprises or is defined by primary test setting $x_n^{ref}$, secondary test setting $x_n^{alt}$ and preferred/selected test setting $r_n$. The index n−1 refers to the previous trial T_n−1.

In the user system, the user response to a trial depends on the user preference. Such connection can be modelled via the model of comparative judgement as follows:

$$P(r|x^{ref},x^{alt},f,z=k) = \Phi(f(x^{alt};\theta_k,\Lambda_k) - f(x^{ref};\theta_k,\Lambda_k))^r \cdot \Phi(f(x^{ref};\theta_k,\Lambda_k) - f(x^{alt};\theta_k,\Lambda_k))^{1-r} \quad (7)$$

where $\Phi(\cdot)$ is the cdf of the standard Gaussian distribution, $x^{ref}$ and $x^{alt}$ are two hearing device parameter sets that the user compares, and $z \in \{1, 2, \ldots, K\}$ is the environment/state of the user environment/environment identifier. It is assumed that a user has some uncertainty about his/her choice that is modelled by the additive random noise with the standard Gaussian distribution.

In one or more example fitting agents, the environment data/observed context s is modelled using Gaussian mixture models (GMM), given that there are K possible environments/states of environments:

$$p(s) = \Sigma_z p(z)p(s|z) = \Sigma_{k=1}^K \pi_k \cdot \mathcal{N}(s|\mu_{s,k},\Sigma_{s,k}), \quad (8)$$

where $\pi_k$ are mixing probabilities of the environments and $\mu_{s,k}$ and $\Sigma_{s,k}$ are mean values and covariance matrix of the Gaussian distribution, corresponding to the k'th environment.

Environment probabilities ENVP_k for the K environments, k=1, . . . , K, may be based on the following:

$$p(z_t = k \mid s_t) = \frac{\pi_k \cdot \mathcal{N}\left(s_t \mid \mu_{s,k}, \sum_{k,k}\right)}{\sum_{j=1}^K \pi_j \cdot \mathcal{N}\left(s_t \mid \mu_{s,j}, \sum_{k,j}\right)}, \quad (8A)$$

where $s_t$ is observed signal/context at time step t and $z_t$ is environment at this time step.

The complete hearing device system is optionally defined as a sequence of distributions $\{P_t^a, P_t^u\}$:

$$P_t^a \triangleq P_t^a = \sum_{z_t \in \{1,2,\ldots,K\}} \delta(x_{k,t}^{ref} - x_{k-t-1}^{alt})^{r_t-1} \cdot \delta(x_{k,t}^{ref} - x_{k,t-1}^{ref})^{1-r_{t-1}} \cdot \quad (9)$$

$$\int p(x_t^{alt}, \Lambda_t, z_t \mid r_1^{t-1}, \{\theta, \Lambda\}_1^{t-1}, \{x^{ref}, x_{alt}\}_1^{t-1}, s_1^t) d\Lambda_{k,t}$$

$$P_t^u \triangleq Q_t^w = \sum_{z_t \in \{1,2,\ldots,K\}} \int \int p(\theta_t, \Lambda_t, z_t \mid r_1^{t-1}, \{\theta, \Lambda\}_1^{t-1}, \{x^{ref}, x^{alt}\}_1^{t-1}, s_1^t) \cdot$$

$$P(r_t \mid \theta_1^t, \Lambda_1^t, z_1^t, s_1^t, r_1^{t-1}, \{x^{ref}, x^{alt}\}_1^t) d\theta_t d\Lambda_t$$

The generative distributions of the fitting agent defined by a sequence of $P_t^a$ describes the generative process for the next trial $\{x_t^{ref}, x_t^{alt}\}$ as a weighted combination of proposals for possible environments. The generative predictive distribution $P_t^u$ characterizes the user response distribution for some next trial $\{x_t^{ref}, x_t^{alt}\}$. The primary test settings/reference proposals $x_{k,t}^{ref}$ are defined in a deterministic way based on the user response in the previous trial. Secondary test settings/alternative proposals $x_{k,t}^{alt}$ are generated from the user preference posterior, since from the optimization point of view the goal of the fitting agent is get to the optimum as quickly as possible and, thus, provide a better option than a reference proposal, with high probability. Clearly, this option would correspond to the user preference or the fitting agent estimate of it.

Finally, the fitting agent strategy for the sequential trial design in the hearing device system, defined by these distributions $\{P_t^a, P_t^u\}$, may be to generate a sequence of trials t=1, 2, . . . , T, based on the history of interactions with the user in some environments according to the following rule, where $I(\cdot;\cdot)$ denotes mutual information:

$$\{x_t^{ref}, x_t^{alt}\} = \arg\max_{\{x^{ref}, x^{alt}\}: P_t^a} \sum_{z_t \in \{1,2,\ldots,K\}} p(z_t \mid s_t) \quad (10)$$

$$I(R; \theta_t \mid z_1^t, s_1^t, R_1^{t-1}, \{\theta, \Lambda\}_1^{t-1}, \{x^{ref}, x^{alt}\}_1^{t-1}, \{x^{ref}, x^{alt}\})$$

In order to generate required trials, the fitting agent has to assess the user model first. Hence, the fitting agent has to sequentially assign predicted distribution $Q_t$, associated with the user model such that the difference between $Q_t$, and the true distribution of the user response is minimized for all system interactions, and this difference is given by the normalized weighted KL-divergence after T interactions:

$$D(Q, \{x^{ref}, x^{alt}\}, T) \triangleq \frac{1}{T} \int \int w(\theta, \Lambda) \mathbb{D}(P_T^u \| Q_T) d\theta d\Lambda \quad (11)$$

with some weighting function $w(\theta, \Lambda)$. For the present hearing device system, defined by $\{P_t^a, P_t^u\} \triangleq \{p_t^a, Q_t^w\}$ as above, this normalized KL-divergence may be given by the following expression:

$$D(Q^w, \{x^{ref}, x^{alt}\}, T) = \quad (12)$$
$$\frac{1}{T} \sum\nolimits_{z_t \in \{1,2,\ldots,K\}} p(z_t | s_t) I(R; \theta | z_1^t, s_1^t, R_1^{t-1}, \{\theta, \Lambda\}_1^{t-1}, \{x^{ref}, x^{alt}\}_1^t),$$

where $Q_t^w$, $t=1, 2, \ldots, T$ are distributions minimizing the normalized weighted KL-divergence, and the weighting distribution corresponds to the posterior distribution of the user preference function parameters.

It is seen that the metric in (12) can be written as a sum of mutual information for each interaction step and may characterize the fitting agent uncertainty about the user system. Therefore, the fitting agent goal of generating informative trials (test setting) is translated into finding a trial/test setting that can maximally reduce the remaining system uncertainty. This metric also allows efficient monitoring of the system performance.

Finally, after the fitting agent strategy has been defined, the posterior of the user preference(s), $p(\theta_t, \Lambda_t, z_t | r_1^{t-1}, \{\theta, \Lambda\}_1^{t-1}, \{x^{ref}, x^{alt}\}_1^{t-1}, s_1^t)$ must be learned. This step is also a part of the fitting agent strategy, as the posterior of the user preference is also the weighting distribution used in the generative predictive user response distribution. In one or more example fitting agents, GMM is used to estimate the environment state and then Bayesian variational inference is optionally used to further infer the user preference for hearing device parameters for the K environments.

In one or more example fitting agents, to obtain environment data comprises to obtain audio data and optionally determining the environment data based on the audio data and/or including the audio data in the environment data. In other words, one or more processors of the fitting agent may be configured to obtain audio data and determining the environment data or at least one or more environment parameters based on the audio data. Audio data may comprise first audio data representing or being indicative of audio recorded by one or more microphones of a hearing device of the user. Audio data may comprise second audio data representing or being indicative of audio recorded by one or more microphones of an accessory device or accessory devices of the user. Audio data may comprise third audio data representing or being indicative of audio wirelessly transmitted to a hearing device of the user. For example, the fitting agent may be configured to classify the environment based on hearing device audio and set one or more environment identifiers and/or environment probabilities of the environment data accordingly.

In one or more example fitting agents, to obtain environment data comprises to obtain context data and optionally determining the environment data based on the context data and/or including the context data in the environment data. In other words, one or more processors of the fitting agent may be configured to obtain context data and optionally determining the environment data based on the context data. Context data may be indicative of the context in which the user is in, such as indicative of a user's location, position, movement, temperature, pulse, or other data relevant for the environment. For example, the context data may comprise location data, e.g. GPS coordinates, and/or movement data, such as accelerometer data. The context data may comprise calendar data, and the environment data may be based on the calendar data. The context data may comprise sensor data, e.g. from one or more sensors of an accessory device and/or from one or more sensors of the hearing device. The context data may comprise hearing device data transmitted from the hearing device, such as one or more program identifiers, one or more operating parameters, and/or one or operating mode identifiers of the hearing device.

In one or more example fitting agents, to obtain environment data comprises to receive user input indicative of the environment, e.g. via a user interface of an accessory device. Thus, the user may select and indicate the present environment via accessory device, e.g. from a list of environments presented on a touch-display of the accessory device.

In one or more example fitting agents, the one or more processors are configured to obtain a first environment probability of a first environment and/or a second environment probability of a second environment based on the environment data, and wherein to obtain a test setting and/or to update the user model is optionally based on the first environment probability and/or the second environment probability. In other words, one or more processors of the fitting agent may be configured to obtain, such as one or more of determine, estimate, receive, and retrieve, a first environment probability also denoted ENVP_1 of a first environment ENV_1 and/or a second environment probability ENVP_2 of a second environment ENV_2, and optionally obtain a test setting and/or update the user model, such as the first user preference function and/or the second user preference function, based on the first environment probability and/or the second environment probability. The environment data optionally comprises an environment probability ENVP_k of or associated with each environment ENV_k of the K environments, where an environment probability ENVP_k is a probability of the present environment being the corresponding environment ENV_k. For example, ENVP_2=0.5 may indicate a probability of 0.5 that the present environment is the second environment ENV_2. For example, ENVP_2=1.0 may indicate that the present environment is the second environment ENV_2.

In other words, the fitting agent, such as one or more processors of the fitting agent may be configured to obtain, such as one or more of determine, estimate, receive, and retrieve one or more environment probabilities, such as K environment probabilities, indicative of probability that the present environment is a corresponding environment, e.g. based on the environment data, such as one or more environment parameters.

In one or more exemplary fitting agents, the environment probabilities are given by equation 8A.

The first environment probability may be indicative of a probability that the present environment is a first environment. The first environment may be an environment of a first type, such as an environment characterized by a low SNR and high sound level/power, such as a cocktail party or a concert.

The second environment probability may be indicative of a probability that the present environment is a second environment. The second environment may be an environment of a second type, such as an environment characterized by low SNR and medium sound level/power.

In one or more example fitting agents, the plurality of user preference functions comprises K user preference functions, wherein K is 2, 3, or larger than 3. The number K of user preference functions may be in the range from 5 to 25, such as from 5 to 10, e.g. 7. In one or more example fitting agents, to update the user model comprises to select a user preference function to be updated from the K user preference functions based on the environment data and update a posterior of the parameters of the user preference function to be updated based on the test setting and the user input of preferred test setting.

In one or more example fitting agents, to update the user model comprises to select a plurality of user preference functions, such as 2, 3, 4, or more to be updated from the K user preference functions based on the environment data and update posteriors or posterior distributions of the parameters of the plurality of user preference functions to be updated based on the test setting and the user input of preferred test setting. In one or more example fitting agents, to update the user model comprises to update the K user preference functions and parameter distributions associated therewith, or to update the user preference functions and parameter distributions associated therewith having an environment probability larger than 0.

In one or more example fitting agents, to obtain environment data comprises to determine an environment identifier and/or to obtain one or more environment probabilities, such as K environment probabilities, e.g. using a Gaussian mixture model. To update the user model may be based on the environment identifier and/or one or more environment probabilities, such as environment probabilities for environments ENV_k, k=1, 2, . . . , K. For example, to update the user model based on the environment identifier may comprise to select a user preference function and associated parameter distribution for update based on or in accordance with the environment identifier and update the user preference function and associated parameter distribution selected for update based on the preferred test setting and optionally the non-preferred test setting.

In one or more example fitting agents, the fitting agent is configured to determine whether a test criterion based on the environment data is satisfied, wherein the fitting agent is configured to, in accordance with a determination that the test criterion is satisfied, perform: obtain a test setting comprising a primary test setting and a secondary test setting for the hearing device; present the test setting to the hearing device user; obtain a user input of a preferred test setting indicative of a preference for either the primary test setting or the secondary test setting; and update the user model based on hearing device parameters of the preferred test setting and the environment data. Accordingly, a test criterion may be used to determine, when a user's input is needed to improve the accuracy of the user preference functions. Hereby is provided for efficient and to-the-point training of the user preference functions, e.g. such that a user is only prompted for input when needed, thereby reducing and/or optimizing the number of user interactions.

In one or more example fitting agents, the test criterion is based on an uncertainty metric indicative of user preference uncertainty in the present environment. For example, the test criterion may be satisfied or at least partly satisfied if it is determined that the user preference function associated with the present environment is not precise enough, e.g. has a high degree of uncertainty, for example being reflected in an uncertainty metric being larger than a threshold.

In one or more example fitting agents, to obtain a test setting comprising a primary test setting and a secondary test setting for the hearing device comprises to determine the secondary test setting based on the environment data, e.g. as described above in relation to equations (10)-(12).

In one or more example fitting agents, the fitting agent is configured to determine and update hearing device parameters of the hearing device based on the updated user model and/or the environment data, such as environment probabilities of the environment data.

It is noted that descriptions and features of fitting agent functionality also applies to methods and vice versa.

FIG. 1 is an overview of a hearing system with a fitting agent according to the present disclosure. The hearing system comprises a hearing device 2, an accessory device 4, and optionally a server device/fitting device 5. The hearing device 2 comprises a transceiver module 6 for (wireless) communication with the accessory device 4 and optionally a contralateral hearing device (not shown in FIG. 1). The transceiver module 6 comprises antenna 8 and transceiver 10, and is configured for receipt and/or transmission of wireless signals via wireless connection 11 to the accessory device 4. The accessory device 4 is configured for receipt and/or transmission of wireless signals via wireless connection 11A to the server device/fitting device 11A. The hearing device 2 comprises a set of one or a plurality of microphones comprising a first microphone 12 for provision of a first microphone input signal 14; a processor 16 for processing input signals including the first microphone input signal 14 according to one or more hearing device parameters and providing an electrical output signal 18 based on input signals; an optional user interface 20 connected to the processor 16; and a receiver 22 for converting the electrical output signal 18 to an audio output signal.

The accessory device 4 is a smartphone and comprises a user interface 24 comprising a touch display 26, a processor (not shown), and a memory (not shown).

In the hearing device system 1, the fitting agent 27 is an application installed in the memory of the accessory device 4.

The fitting agent 27 is a fitting agent for update of a user model for a hearing device user and/or one or more of optimizing, determining, fitting, tuning, and modelling hearing device parameters of a hearing device. The fitting agent 27 comprises one or more processor configured to initialize a user model comprising a plurality of user preference functions and associated user response distributions, wherein each user preference function $f(x; \theta_k, \Lambda_k)$ is associated with a k'th environment (k=1, 2, . . . , K); obtain environment data indicative of a present environment; obtain a test setting comprising a primary test setting x_ref and a secondary test setting x_alt for the hearing device; present the test setting to the hearing device user e.g. via wireless connection 11; obtain/detect a user input r of a preferred test setting indicative of a preference for either the primary test setting x_ref or the secondary test setting x_alt; and update the user model, such as the user preference function $f(x; \theta, \Lambda)$ and/or a user response model (user response distribution and parameter distribution) based on hearing device parameters of the preferred test setting, such as one or more, e.g. all of r, x_ref, and x_alt, and the environment data.

The fitting agent 27 implemented in the accessory device 4 is configured to update the user model, such as a plurality of user preference functions of the user model, based on the primary test setting, the secondary test setting, the preferred test setting, and the environment data, such as environment probabilities of environments. In other words, the fitting agent is configured to update the user model based on hearing device parameters of the preferred test setting and the environment data. To update the user model may comprise updating the user preference models and the user response models based on the primary test setting, the secondary test setting, the preferred test setting, and the environment data. The fitting agent 27/accessory device 4 may be configured to transmit the primary test setting, the secondary test setting, and the preferred test setting to server device 5 that updates the user model and transmits the updated user model to the fitting agent 27/accessory device 4. Thus, fitting agent 27/accessory device 4 may be configured to receive the updated model from the server device 5. In other words, the fitting agent 27 may be distributed on accessory device 4 and one or more of hearing device 2 and server device 5. Thus, the fitting agent 27 may comprise a first part 27A implemented in accessory device 4, optional second part 27B implemented in server device, and optional third part 27C implemented in hearing device 2, such as in processor 16.

In one or more example fitting agents including fitting agent 27, 27A, 27B, 27C, to update the user model comprises to determine posteriors of parameters of the user preference functions, e.g. based on a previous parameter posteriors, such as the last or current parameter posteriors, the preferred test setting, and a non-preferred test setting. To determine a posterior of parameters of a user preference function may comprise to determine or update $\theta_k$ being the maximizing argument of the k'th $f$ and/or to determine or update $\Lambda_k$ indicative of or characterizing user sensitivity to hearing device parameter changes in the k'th environment. To determine the parameter posterior optionally comprises to apply sequential estimation in the fitting agent 27, 27A, 27B, 27C. Thus, the fitting agent 27, 27A, 27B, 27C is optionally configured to determine the parameter posterior based on only the previous user model and (r, x_ref, x_alt, s).

In one or more example fitting agents including fitting agent 27, 27A, 27B, 27C, to obtain environment data comprises to obtain audio data and determining the environment data based on the audio data. For example, microphone 12 of the hearing device 2 may provide audio data representative of the sound received by the microphone 12, wherein the audio data can be transmitted to the accessory device 4 wherein the fitting agent 27, 27A of the accessory device 4 is configured for determining the environment data based on the audio data from the hearing device and/or wherein the fitting agent 27C of the hearing device 2 is configured for determining the environment data or at least a part of the environment data based on the audio data from microphone 12. The environment data determined by fitting agent 27C of the hearing device 2 is transmitted to the fitting agent 27A of the accessory device 4 for further processing.

In one or more example fitting agents including fitting agent 27, 27A, 27B, 27C, to obtain environment data comprises to obtain context data, e.g. from one or more sensors of the hearing device 2 and/or accessory device 4, and determining the environment data based on the context data. Determining the environment data may be based on the audio data and the context data. In one or more example fitting agents including fitting agent 27, 27A, 27B, 27C, to obtain context data comprises to obtain context data from one or more applications, such as a calendar application, of the accessory device 4.

In one or more example fitting agents including fitting agent 27, 27A, 27B, 27C, the environment data comprises a first environment probability of a first environment and/or a second environment probability of a second environment, and wherein to update the user model is based on the first probability and/or the second probability.

In one or more example fitting agents including fitting agent 27, 27A, 27B, 27C, the plurality of user preference functions comprises K user preference functions, wherein K is larger than 3, such as 5, 6, 7, 8 or more, and wherein to update the user model comprises to update posteriors of the parameters of the K user preference functions (or a subset thereof) based on the test setting, the user input of preferred test setting, and optionally one or more or the environmental data and the environment probabilities.

In one or more example fitting agents including fitting agent 27, 27A, 27B, 27C, the fitting agent is configured to obtain, such as determine one or more environment probabilities, such as an environment probability for each environment ENV_k, k=1, 2, . . . , K, and/or an environment identifier using a Gaussian mixture model and wherein to update the user model is optionally based on the environment identifier and/or the environment probabilities.

In one or more example fitting agents including fitting agent 27, 27A, 27B, 27C, the fitting agent is configured to determine whether a test criterion based on the environment data is satisfied. The fitting agent 27, 27A, 27B, 27C may be configured to, in accordance with a determination that the test criterion is satisfied, perform: obtain a test setting comprising a primary test setting and a secondary test setting for the hearing device; present the test setting to the hearing device user; obtain a user input of a preferred test setting indicative of a preference for either the primary test setting or the secondary test setting; and update the user model based on hearing device parameters of the preferred test setting and the environment data. The test criterion may be based on an uncertainty metric indicative of user preference uncertainty in the present environment.

In one or more example fitting agents including fitting agent 27, 27A, 27B, 27C, to obtain a test setting comprising a primary test setting and a secondary test setting for the hearing device comprises to determine the secondary test setting based on the environment data.

In one or more example fitting agents including fitting agent 27, 27A, 27B, 27C, the fitting agent is configured to determine and update hearing device parameters of the hearing device based on the updated user model and optionally the environment data.

In an implementation including accessory device 4, the fitting agent 27/accessory device 4 may be configured to send a control signal 30 to the hearing device 2, the control signal 30 being indicative of the primary test setting and the secondary test setting, thus enabling the hearing device 2 to output test signals accordingly.

The hearing device 2 (processor 16) is optionally configured to output a primary test signal according to the primary test setting via the receiver 22 and a secondary test signal according to the secondary test setting via the receiver 22.

The fitting agent 27, 27A, 27C (hearing device 2 (processor 16) and/or the accessory device 4) is configured to detect a user input of a preferred test setting indicative of a preference for either the primary test setting or the secondary test setting, e.g. by detecting a user input on user interface 20 or by detecting a user selection of one of a primary virtual button 32 (primary test setting is preferred) and a secondary virtual button 34 (secondary test setting is preferred) on the user interface 24 of accessory device 4.

It is to be noted that the fitting agent 27, 27A, 27B, 27C may be configured to detect a user input of a preferred test setting indicative of a preference for either the primary test setting or the secondary test setting, e.g. by receiving a wireless input signal from a secondary accessory device, such as smartwatch comprising a user interface. Thereby, a more convenient user input is provided for, which in turn increases the user friendliness of the fitting agent.

A user may initiate the method/update of the user model by pressing start button 28 on the user interface of accessory device 24. In other words, the fitting agent may detect user input indicative of start and perform the method/update of the user model in accordance with detection of the user input indicative of start.

In an implementation including accessory device 4, the accessory device 4 may be configured to send a control signal 38 to the hearing device 2, the control signal 38 being indicative of the hearing device parameters of the preferred test setting, thus enabling the hearing device to update and apply preferred hearing device parameters in the hearing device.

Figure 2:
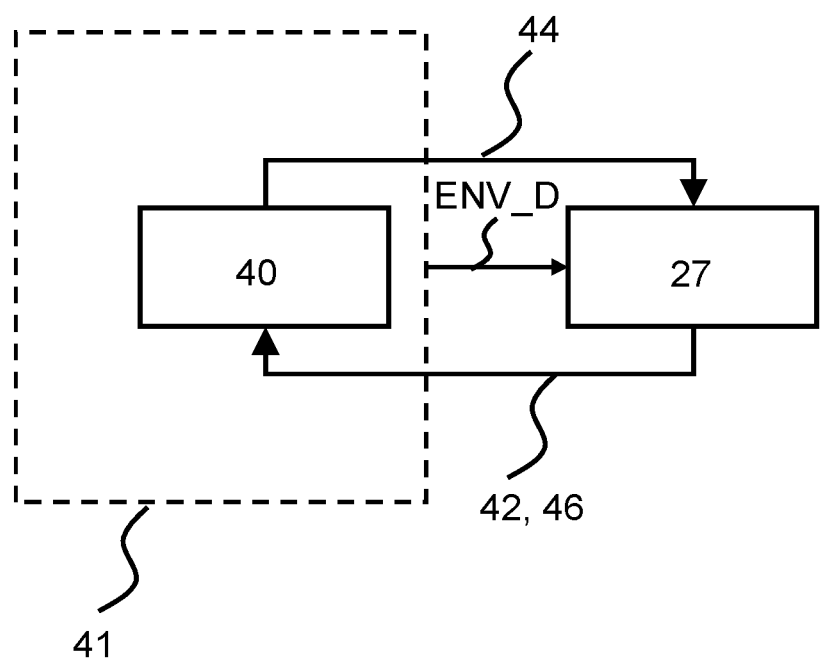
FIG. 2 illustrates interaction between a user and a fitting agent.

FIG. 2 illustrates interaction between a user 40 in an environment 41 and a fitting agent 27. The fitting agent 27 obtains environment data indicative of the present environment 41, e.g. based on audio data and/or context data from one or more hearing device worn by user 40, from user providing user input to fitting agent, from accessory device 25 microphone, sensors, and/or applications. For each interaction or trial indexed with index n, the fitting agent generates a primary test setting $x_n^{ref}$ and a secondary test setting $x_n^{alt}$ and presents 42 the test settings $x_n^{ref}$ and $x_n^{alt}$ for the user, e.g. by controlling hearing device for outputting primary test signal and secondary test signal respectively according to and indicative of the primary test setting and the secondary test setting. The user evaluates the two test settings $x_n^{ref}$ and $x_n^{alt}$, and the fitting agent 27 receives and detects the user's response 44, $r_n$ indicative of the preferred test setting of the primary test setting and the secondary test setting. The fitting agent updates the user model based on environment data, $r_n$, $x_n^{ref}$, and $x_n^{alt}$. The fitting agent generates n+1'th trial $\{x_{n+1}^{ref}; x_{n+1}^{ref}\}$, by determining the primary test setting $x_{n+1}^{ref}$ of the n+1'th trial based on the preferred test setting of the n'th trial and environment probabilities of the n+1'th trial, determines secondary test setting $x_{n+1}^{alt}$ and presents 46 the test settings $x_{n+1}^{ref}$ and $x_{n+1}^{alt}$ for the user.

Figure 3:
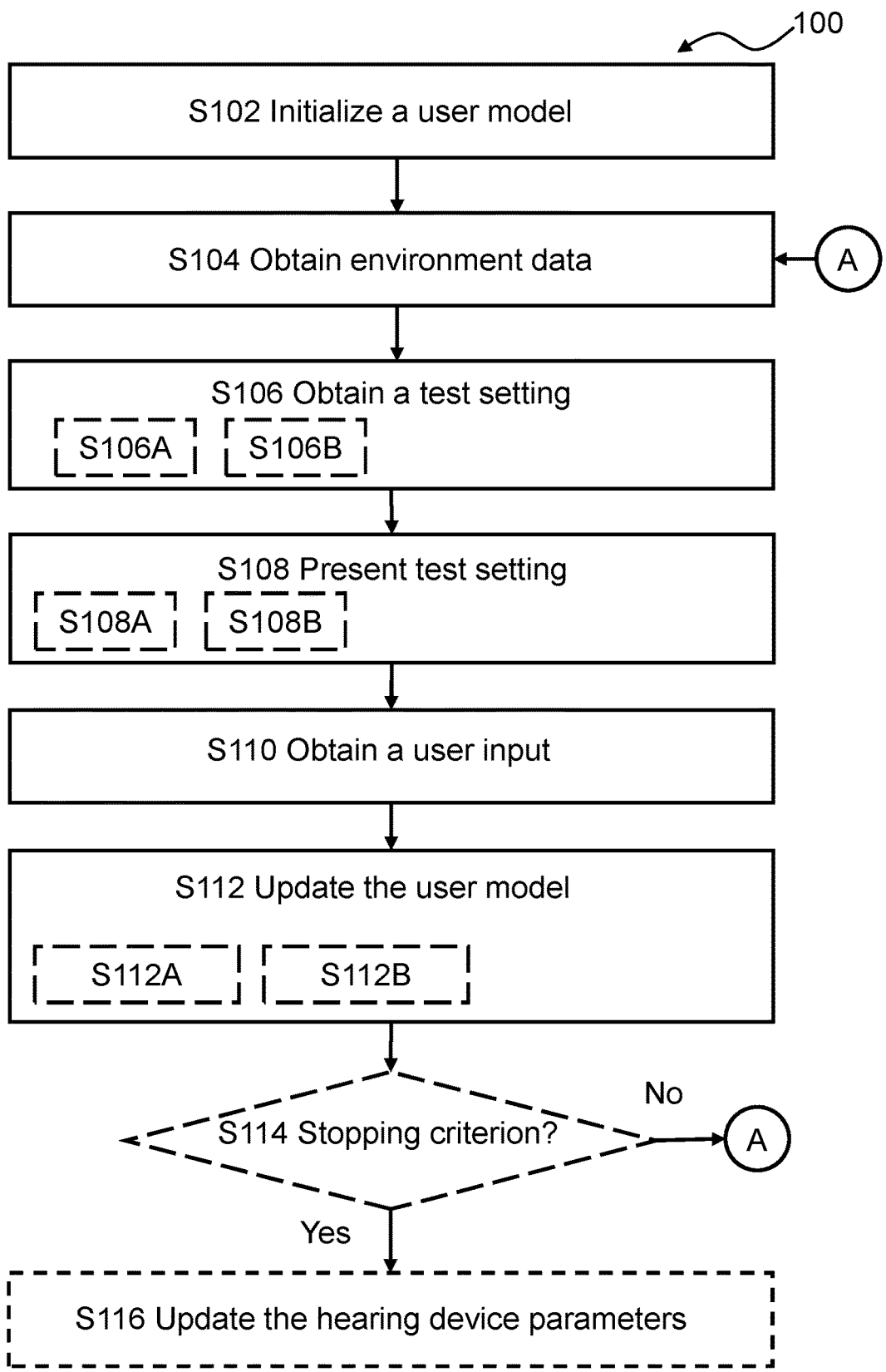
FIG. 3 is a flow diagram of an exemplary method according to the present disclosure.

FIG. 3 is a flow diagram of an exemplary method according to the present disclosure. The method 100 is a method of updating a user model for a hearing device user and/or for one or more of optimizing, determining, fitting, tuning, and modelling, such as determining hearing device parameters of a hearing device, wherein the method comprises initializing S102 a user model comprising a plurality of user preference functions and associated user response distributions, wherein each user preference function is associated with an environment; obtaining S104 environment data indicative of a present environment; obtaining S106 a test setting comprising a primary test setting S106A and a secondary test setting S106B for the hearing device; presenting S108 the test setting to the hearing device user including outputting S108A a primary test signal in accordance with or based on the primary test setting and outputting S108B a secondary test signal in accordance with or based on the secondary test setting; obtaining S110 a user input of a preferred test setting indicative of a preference for either the primary test setting or the secondary test setting; and updating S112 the user model based on hearing device parameters of the preferred test setting and non-preferred test setting and the environment data. Updating S112 the user model optionally comprises updating S112A a plurality of, such as a subset of or all of, the user preference functions of the user model. Updating S112 the user model optionally comprises updating S112B a plurality of, such as all of, the predictor/user response models of the user model.

In the method 100, updating S112 the user model may comprise determining S112A posteriors of the parameters of user preference functions of the user model based on a previous or latest parameter posterior, the preferred test setting, the non-preferred test setting, and the environment data.

The method 100 optionally comprises determining S114 whether a stopping criterion is satisfied and updating S116 hearing device parameters of hearing device in accordance with the updated model, e.g. as described above in relation to the fitting agent. The method 100 optionally proceeds to S104 if it is determined that the user model has not been sufficiently updated (stopping criterion is not satisfied), i.e. further trials and user input on test settings is desired or required for an accurate and precise modelling of the user preference functions of the user model.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering.

Memory may be one or more of a buffer, a flash memory, a hard drive, a removable media, a volatile memory, a non-volatile memory, a random access memory (RAM), or other suitable device. In a typical arrangement, memory may include a non-volatile memory for long term data storage and a volatile memory that functions as system memory for the processor. Memory may exchange data with processor over a data bus. Memory may be considered a non-transitory computer readable medium.

Memory may be configured to store information in a part of the memory.

Furthermore, the labelling of a first element does not imply the presence of a second element and vice versa.

It may be appreciated that FIGS. 1-3 comprise some modules or operations which are illustrated with a solid line and some modules or operations which are illustrated with a dashed line. The modules or operations which are comprised in a solid line are modules or operations which are comprised in the broadest example embodiment. The modules or operations which are comprised in a dashed line are example embodiments which may be comprised in, or a part of, or are further modules or operations which may be taken in addition to the modules or operations of the solid line example embodiments. It should be appreciated that these operations need not be performed in order presented. Furthermore, it should be appreciated that not all of the operations need to be performed. The exemplary operations may be performed in any order and in any combination.

It is to be noted that the word "comprising" does not necessarily exclude the presence of other elements or steps than those listed.

It is to be noted that the words "a" or "an" preceding an element do not exclude the presence of a plurality of such elements.

It should further be noted that any reference signs do not limit the scope of the claims, that the exemplary embodiments may be implemented at least in part by means of both hardware and software, and that several "means", "units" or "devices" may be represented by the same item of hardware.

The various exemplary methods, devices, and systems described herein are described in the general context of method steps processes, which may be implemented in one aspect by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Generally, program modules may include routines, programs, objects, components, data structures, etc. that perform specified tasks or implement specific abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

Although features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES 1 hearing device system
2 hearing device
4 accessory device
5 server device
6 transceiver module
8 antenna
10 transceiver
11 wireless connection between hearing device and accessory device
11A wireless connection between accessory device and server device
12 first microphone
14 first microphone input signal
16 processor
18 electrical output signal
20 user interface
22 receiver
24 user interface of accessory device
26 touch display
27 fitting agent
27A first part of fitting agent
27B second part of fitting agent
27C third part of fitting agent
28 (virtual) start button
30 control signal indicative of primary and secondary test setting
32 primary virtual button
34 secondary virtual button
38 control signal indicative of the hearing device parameters of the preferred test setting
40 user
41 environment
42 n'th trial, test settings $x_n^{ref}$ and $x_n^{alt}$
44 user response to n'th trial
46 n+1'th trial, test settings $x_{n+1}^{ref}$ and $x_{n+1}^{alt}$
100 Method of updating a user model for a hearing device user and/or for determining hearing device parameters of a hearing device
S102 initializing a user model
S104 obtaining environment data
S106 obtaining a test setting
S106A obtaining a primary test setting
S106B obtaining a secondary test setting
S108 presenting the test setting to the hearing device user
S108A outputting a primary test signal
S108B outputting a secondary test signal
S110 obtaining a user input
S112 updating the user model
S112A determining posteriors of parameters of the user preference functions of the user model based on a previous parameter posterior, the preferred test setting, a non-preferred test setting, and the environment data
S114 determining whether stopping criterion is satisfied
S116 updating the hearing device parameters
ENV_D environment data

The invention claimed is:

1. A fitting agent for a hearing device that is configured to be worn by a hearing device user, the fitting agent comprising one or more processing units configured to:
access a user model comprising a plurality of user preference functions and associated user response distributions, wherein the user preference functions are associated with respective environments;
obtain environment data indicative of a present environment;
obtain a user input indicative of a preferred test setting; and
update the user model based on the environment data and hearing device parameters associated with the preferred test setting.

2. The fitting agent according to claim 1, wherein the fitting agent is configured to obtain audio data, and wherein the one or more processing units are configured to obtain the environment data by determining the environment data based on the audio data.

3. The fitting agent according to claim 1, wherein the one or more processing units are configured to obtain the environment data by determining the environment data based on context data.

4. The fitting agent according to claim 1, wherein the one or more processing units are configured to obtain a first environment probability of a first environment, and a second environment probability of a second environment, based on the environment data.

5. The fitting agent according to claim 4, wherein the fitting agent is configured to determine a test setting based on the first environment probability and the second environment probability.

6. The fitting agent according to claim 4, wherein the one or more processing units are configured to update the user model based on the first environment probability and the second environment probability.

7. The fitting agent according to claim 1, wherein the plurality of user preference functions comprises K user preference functions, wherein K is larger than 3.

8. The fitting agent according to claim 7, wherein the one or more processing units are configured to update the user model by selecting one of the user preference functions to be updated based on the environment data.

9. The fitting agent according to claim 8, wherein the one or more processing units are configured to update the user model by updating a posterior of parameters of the selected one of the user preference functions.

10. The fitting agent according to claim 1, wherein the one or more processing units are configured to obtain the environment data by determining an environment identifier using a Gaussian mixture model.

11. The fitting agent according to claim 10, wherein the user model is based on the environment identifier.

12. The fitting agent according to claim 1, wherein the fitting agent is configured to determine whether a test criterion based on the environment data is satisfied, wherein the fitting agent is configured to, in accordance with a determination that the test criterion is satisfied:
obtain the user input indicative of the preferred test setting; and
update the user model based on the environment data.

13. The fitting agent according to claim 12, wherein the test criterion is based on an uncertainty metric indicative of user preference uncertainty in the present environment.

14. The fitting agent according to claim 1, wherein the fitting agent is configured to update the hearing device based on the updated user model.

15. The fitting agent according to claim 1, wherein the fitting agent is configured to obtain a primary test setting and a secondary test setting for the hearing device, and causes the primary test setting and the secondary test setting to be presented to the hearing device user.

16. The fitting agent according to claim 15, wherein the preferred test setting is either the primary test setting or the secondary test setting.

17. The fitting agent according to claim 15, wherein the fitting agent is configured to obtain the secondary test setting by determining the secondary test setting based on the environment data.

18. A method for updating a user model for a hearing device user, wherein the method comprises:
accessing the user model comprising a plurality of user preference functions and associated user response distributions, wherein the user preference functions are associated with respective environments;
obtaining environment data indicative of a present environment;
obtaining a user input indicative of a preferred test setting that is either the primary test setting or the secondary test setting; and
updating the user model based on the environment data and hearing device parameters associated with the preferred test setting.

* * * * *